(12) United States Patent  
Huang

(10) Patent No.: US 8,183,034 B2  
(45) Date of Patent: May 22, 2012

(54) APPARATUS FOR CARBON DIOXIDE-CAPTURE SYSTEM AND USE OF THE SAME

(76) Inventor: Mei-Hua Huang, Taichung (TW)

( * ) Notice: Subject to any disclaimer, the term of this patent is extended or adjusted under 35 U.S.C. 154(b) by 569 days.

(21) Appl. No.: 12/379,667

(22) Filed: Feb. 26, 2009

(65) Prior Publication Data

US 2010/0216218 A1     Aug. 26, 2010

(51) Int. Cl.  
*C12C 1/15* (2006.01)

(52) U.S. Cl. ............... 435/291.4; 435/283.1; 435/286.5; 436/52

(58) Field of Classification Search .......................... None  
See application file for complete search history.

(56) References Cited

U.S. PATENT DOCUMENTS 4,159,009 A * 6/1979 Friedman ...................... 119/218

* cited by examiner

*Primary Examiner* — Nelson C. Yang  
(74) *Attorney, Agent, or Firm* — Andrews Kurth LLP; Michael Ye

(57) ABSTRACT

An apparatus for carbon dioxide-capture system has a cultivating vessel and at least one basking mechanism. The cultivating vessel has a reservoir for accommodating alga culture. The basking mechanism is mounted in the reservoir of the cultivating vessel and has multiple trays and a circulating mechanism. The trays are imbricately mounted on the basking mechanism with predetermined intervals and each has at least one spout formed at an overlap with an adjacent tray. The circulating mechanism is mounted between the trays and the reservoir. The alga culture is pumped into one tray by the circulating mechanism, flows through the spout into another tray, enhancing a rate of carbon fixation by alga.

7 Claims, 6 Drawing Sheets

APPARATUS FOR CARBON DIOXIDE-CAPTURE SYSTEM AND USE OF THE SAME

BACKGROUND OF THE INVENTION

1. Field of the Invention

The present invention relates to an apparatus for use in a carbon dioxide-capture system, particularly to an apparatus having a basking mechanism allowing micro-algae to photosynthesize and consume carbon dioxide.

2. Description of the Prior Arts

Increased levels of carbon dioxide in the atmosphere have been shown to cause global warming by researchers. Techniques for fixing, absorbing and converting carbon dioxide are believed to be resolutions for global warming and have international significance.

Conventional methods for separating and capturing carbon dioxide include: chemical absorption, physical absorption, physical adsorption, membrane separation and cryogenic separation. The separated or captured carbon dioxide requires subsequent processes, such as chemical conversion, biological conversion or the like to avoid being returned to the environment.

Besides the aforesaid techniques, other techniques utilize photosynthetic ability of micro algae to separate and capture carbon dioxide. Therefore, carbon dioxide can be used as a resource for artificial culture of micro algae. However, atmospheric $CO_2$ limits growth and concentration of micro-algae so increased concentration of $CO_2$ is required, but stirring is not economically viable under low concentrations. Moreover, an amount of micro algae obtained by artificial culture cannot satisfy industrial application. Therefore, additional organic carbon sources need to be added into the culture to enhance the amount of micro algae obtained, resulting in increased continuous costs of culture.

Accordingly, current techniques are developed to include increasing concentration of carbon dioxide in micro alga cultures to enhance growth rate of micro algae. Some techniques utilize increasing stirring rate to culture medium to enhance the accessibility of algae to carbon dioxide in air. However, such stirring requires energy so raises costs and itself causes carbon emissions. Furthermore, for certain strains of micro algae, stirring the micro alga culture at a high rate during culturing causes abnormality of growth and hinders normal physical development of the micro algae.

Other techniques include directly introducing carbon dioxide into the micro alga culture, resulting in increase of uptake of carbon dioxide by micro algae. However, amount of increase is limited and studies show micro algae can only significantly increase uptake of carbon dioxide during conventional artificial culture under increased pressure. A temporary exposure to a high concentration of carbon dioxide under an increased pressure followed by culture under normal condition can facilitate growth of micro algae. However, to establish a high-pressure environment raises costs and consumes energy, contrary to aims of using photosynthetic micro algae to reduce energy use and carbon dioxide emissions.

Other techniques provide a design for use in a hermetic device to capture processed gaseous exhaust containing carbon dioxide. Costs of either construction or operation of the aforesaid design is too high to be economic. Furthermore, oxygen produced by algae from photosynthesis are dissolved in culture of algae under such a hermetic environment, resulting in negative growth conditions for algae.

To overcome the shortcomings, the present invention provides an apparatus and a method for carbon-dioxide capture to mitigate or obviate the aforementioned problems.

SUMMARY OF THE INVENTION

The main objective of the invention is to provide an apparatus for carbon-dioxide capture utilizing micro algae to perform photosynthesis and use carbon dioxide as a carbon resource for growth thereof. The present invention provides an apparatus for carbon dioxide-capture comprising a cultivating vessel and at least one basking mechanism.

The cultivating vessel has a body. The body has a sidewall and a bottom defining a reservoir for accommodating culture medium.

The at least one basking mechanism is mounted in the reservoir on the bottom of the cultivating vessel and has a frame, multiple trays and a circulating mechanism.

The frame is mounted in the reservoir on the bottom of the cultivating vessel and has a top and a bottom. The bottom of the frame defines a circulating space to allow culture medium to flow through the reservoir.

The trays are imbricately mounted on the frame and each tray has a panel. The panel has at least one through hole, each spout being formed through the panel and opposite to the panel of an adjacent tray, such that culture medium flowing through the spout can drop into the adjacent tray.

The circulating mechanism is mounted in cultivating vessel and the trays and has a pump and an introducing pipe. The pump has an inlet communicating with the reservoir. The introducing pipe is mounted between the pump and basking mechanism and has a distal end, a proximal end at least one orifice formed through the distal end of the pipe and mounted over a corresponding tray of the basking mechanism. The proximal end is further connected to the pump to raise culture medium to the top of the basking mechanism. A method for using an apparatus according to the present invention to capture carbon dioxide comprises (a) placing a micro-alga culture into a reservoir inside a cultivating vessel of an apparatus for carbon dioxide-capturing device as described above in an environment containing carbon dioxide suitable for photosynthesis;

(b) transferring the micro-alga culture into a corresponding tray by the circulating mechanism; and (c) allowing the micro-alga culture to flow through the spout of one tray, dropping into an adjacent tray in sequence, and converging in the reservoir of the cultivating vessel; and Alternatively, (d) agitating the culture medium in the reservoir by the flow-directing mechanism to generate a flow in a desired direction inside the reservoir of the cultivating vessel and to allow the culture medium evenly distributing in the reservoir and effectively absorbing carbon dioxide dissolved in the culture medium; or (e) using a supply pipe to supply a supplement nutrition into the micro alga culture in the reservoir of the cultivating vessel.

When in use, micro-alga culture are transferred into the reservoir of the culturing vessel and mounted in an open carbon dioxide-capture system at atmospheric pressure. The alga culture is pumped into the space in the corresponding tray by the pump, through the introducing pipe, to the tray of the basking mechanism and flow through the spouts. The spouts guide alga culture into subsequent trays as a waterfall forcing air into the alga culture for improved algae growth and converges in the reservoir of the culturing vessel. The alga culture flows into the reservoir circulated in a direction led by the propeller of the flow-directing mechanism. During the processes as described above, micro-algae contact with and absorb carbon dioxide to allow micro-algae undergoing photosynthesis to consume carbon dioxide, grow and also generate oxygen.

Therefore, use of the apparatus present invention to capture carbon dioxide utilize gravity and consume minimal energy, which fits the purpose of lowering consumption of energy and carbon emission. Furthermore, algae can bask in sunshine in the tray of the basking mechanism imbricately mounted on the frame and absorb carbon dioxide during processes as described above, resulting in increased production of algae to satisfy industrial application.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
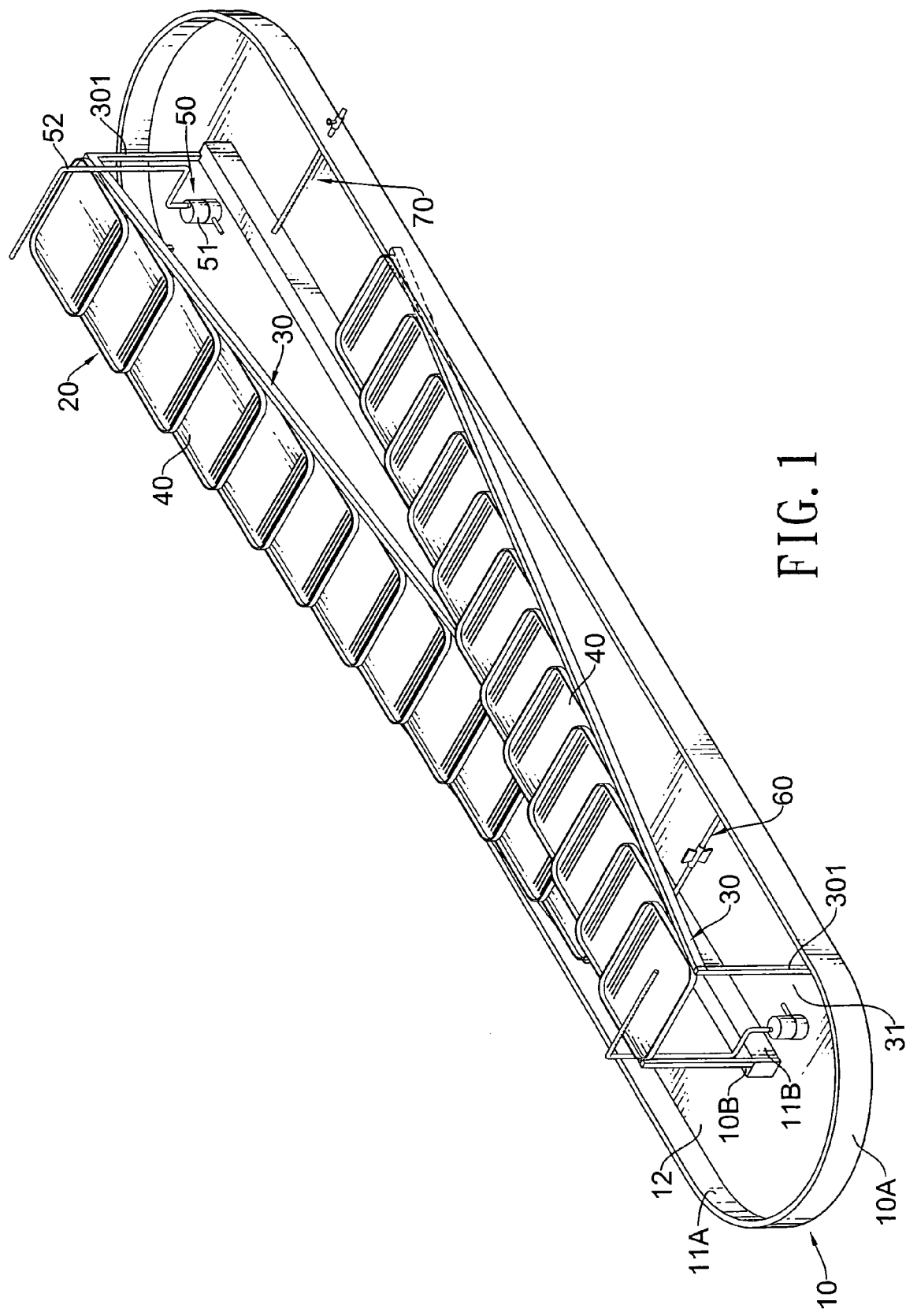
FIG. 1 is a perspective view of a carbon dioxide-capture apparatus in accordance with the present invention.

With reference to FIG. 1, an apparatus for carbon dioxide-capture system in accordance with the present invention comprises a cultivating vessel (10), at least one basking mechanism (20), at least one optional flow-directing mechanism (60) and at least one optional supply pipe (70).

The cultivating vessel (10) has a body (10A) and a barrier (10B). The body (10A) is an open container and has an annular sidewall (11A) and a bottom (12) and may be oblong. The barrier (10B) is mounted on the bottom (12), may be longitudinally mounted in the body (10A) and has two sidewalls (11B). The sidewalls (11A)(11B), the bottom (12) and the barrier (10B) define a reservoir for accommodating a culture medium.

The basking mechanism (20) is mounted in the reservoir on the bottom of the cultivating vessel (10) and has a frame (30), multiple trays (40) and a circulating mechanism (50).

The frame (30) is mounted in the reservoir on the bottom (12) of the cultivating vessel (10), may be mounted between the annular sidewall (11A) of the body (10A) and one of the sidewalls (11B) of the barrier (10B) and has a top, a bottom and two supports (301). The supports (301) extend from the top to the bottom of the frame (30), are attached respectively to the annular sidewall (11A) of the body (10A) and the corresponding sidewall (11B) of the barrier (10B) and define a circulating space (31) to allow the culture medium to flow through. Each support (301) may comprise an upright brace and an inclined brace.

Figure 2:
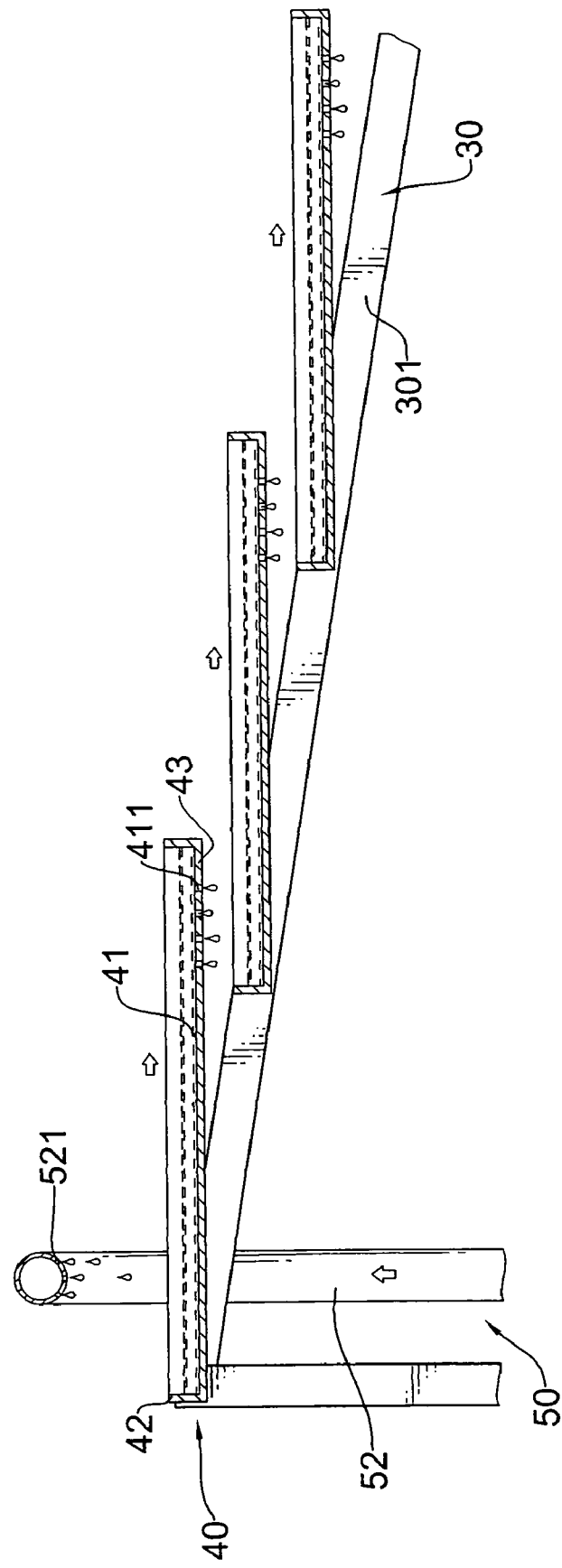
FIG. 2 is an enlarged side view in partial section of a basking mechanism of the apparatus in FIG. 1.
Figure 3:
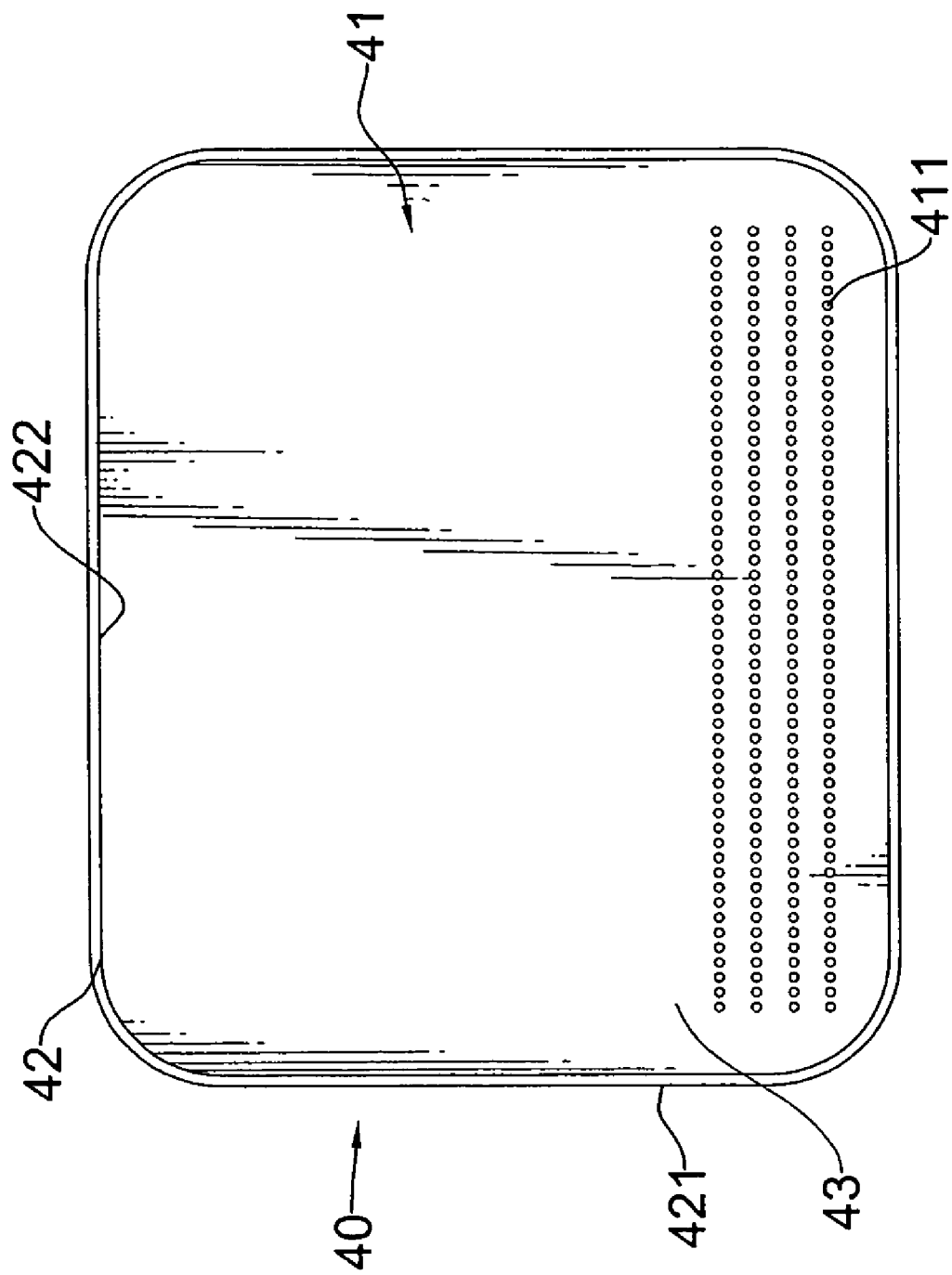
FIG. 3 is a top view of a tray of the basking mechanism of the apparatus in FIG. 2.

With further reference to FIGS. 2 to 3, the trays (40) are open containers, are imbricately mounted on the frame (30) at predetermined intervals. Preferably, the trays (40) are transparent, may be transparent plastic allowing light to penetrate through one tray (40) to another tray (40). Each tray (40) has a panel (41) and an optional rim (42). The panel (41) being attached to the frame (30) has an overlap (43) and at least one spout (411). The overlap (43) of the panel (41) of one tray (40) is disposed above the panel (41) of an adjacent tray (40). The spout (411) of each tray (40) may be a hole, a slot, a lip or the like, is formed through the panel (41) and maybe at the overlap (43) of the panel (41). The rim (42) protrudes from the panel (41) and has an outer surface (421) and an inner surface (422). The outer surface (421) is attached to the frame (30) of the basking mechanism (20) and has two segments oppositely and respectively attached to the two supports (301) of the frame (30) of the basking mechanism (20). The inner surface (422) and the panel (41) define a space for accommodating culture medium.

Figure 4:
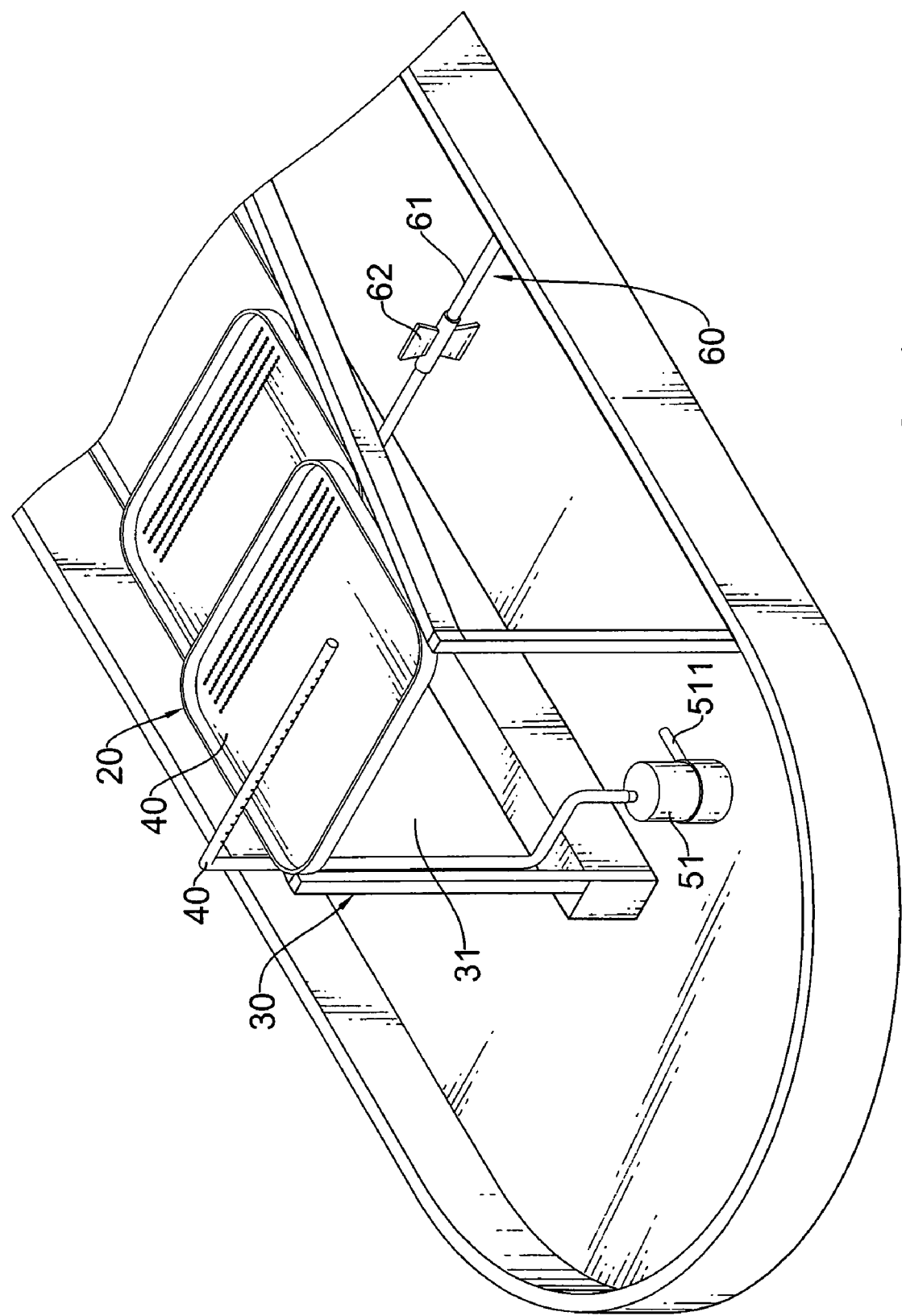
FIG. 4 is enlarged perspective view of the apparatus in FIG. 1.

With further reference to FIG. 4, the circulating mechanism (50) is mounted between the cultivating vessel (10) and the trays (40) and has a pump (51) and an introducing pipe (52). The pump (51) is mounted in the reservoir on the bottom (12) of the cultivating vessel (10) and may be inside the circulating space (31) between the supports (301) of the frame (30). The pump (51) has an inlet (511) and an outlet. The inlet (511) communicates with the reservoir in the cultivating vessel (10) for pumping culture medium from the reservoir in the cultivating vessel (10). The introducing pipe (52) is connected to the outlet of the pump (51) and a corresponding tray (40) of the basking mechanism and has a distal end and at least one orifice (521). The distal end of the introducing pipe (52) is mounted above the corresponding tray (40) of the basking mechanism (20). The at least one orifice (521) is formed through the introducing pipe (52) near the distal end to allow culture medium to pass through the introducing pipe (52) and to drop into the space of the corresponding tray (40).

The flow-directing mechanism (60) may be a stirrer, is attached to the cultivating vessel (10) and is mounted across the reservoir, may be between the annular sidewall (11A) of the body (10A) and one of the sidewalls (11B) of the barrier (10B) and inside the circulating space (31) between the supports (301) of the frame (30). The flow-directing mechanism (60) has a drive shaft (61) and at least one propeller (62). The drive shaft (61) is attached rotatably to the sidewalls (11A)(11B) of the cultivating vessel (10). The at least one propeller (62) is mounted on the drive shaft (61). When the drive shaft (61) is rotated, the propeller (62) is rotated with the drive shaft (61) and may disturb culture medium to generate a flow in a desired direction inside the reservoir of the cultivating vessel (10) and to increase contact between the culture medium and carbon dioxide in air.

Figure 5:
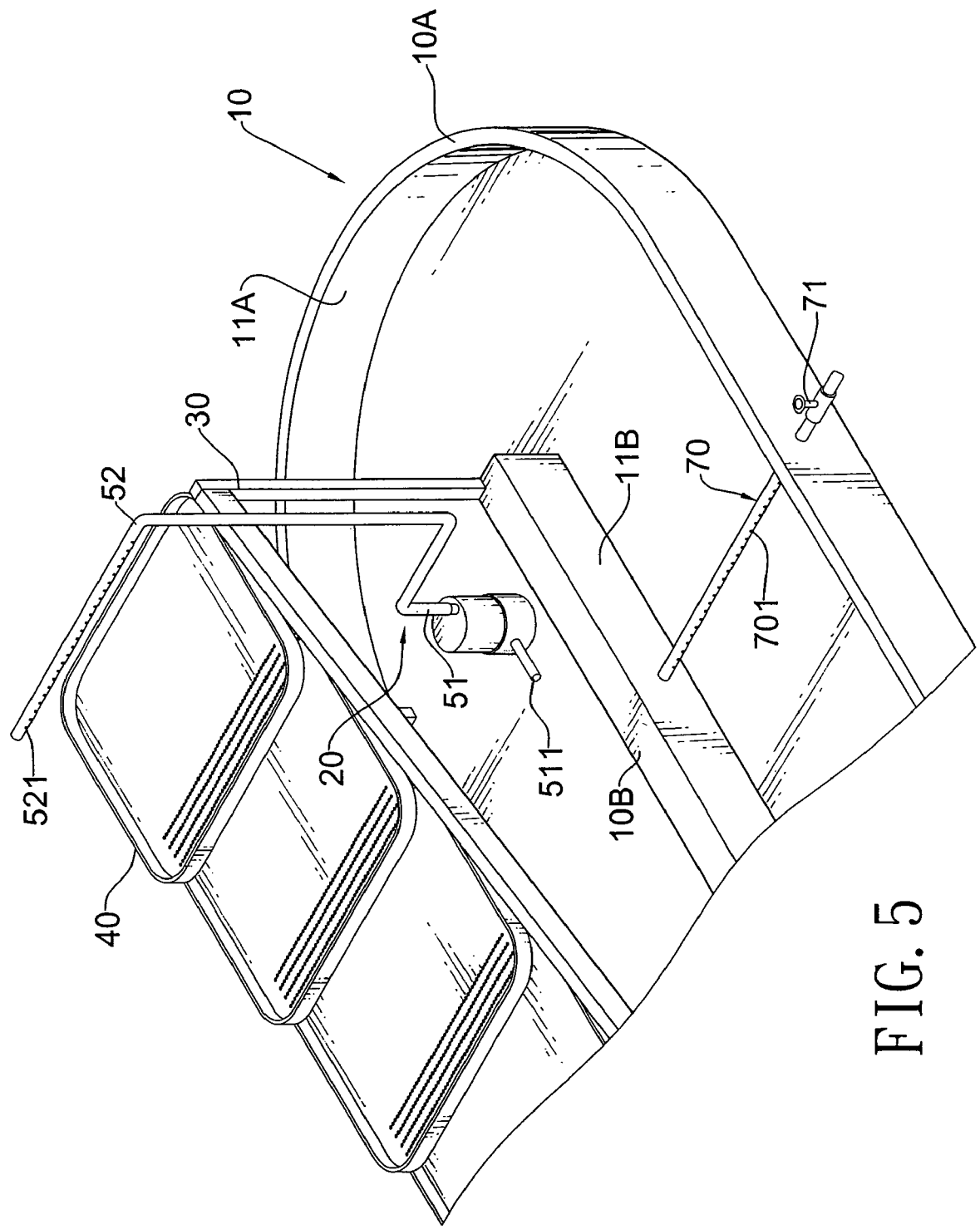
FIG. 5 is another enlarged perspective view of the apparatus in FIG. 1.

With further reference to FIG. 5, the supply pipe (70), is attached to the cultivating vessel (10), may be mounted through the sidewall (11A) of the body (10A) and across the reservoir of the cultivating vessel (10). The supply pipe (70) has a charging end, at least one medium-supplying hole (701) and an optional switch-valve (71) and may be connected to a supply of supplemental nutrition to allow the supplemental nutrition to flow into the reservoir of the cultivating vessel (10). The charging end of the supply pipe (70) is disposed across the reservoir of the cultivating vessel (10), may be in the reservoir of the cultivating vessel (10). The medium-supplying hole (701) may be but is not limited to a slit or an annular aperture and is formed through the charging end of the supply pipe (70). The switch valve (71) is mounted on the supply pipe (70) to control flow of supplemental nutrition.

The apparatus for carbon dioxide-capture system in accordance with the present invention may comprise two basking mechanisms (20) mounted respectively between the sidewalls (11B) of the barrier (10B) and the annular sidewall (11A) of the body (10A), wherein the frames (30) of the two basking mechanisms (20) are oppositely arranged to allow culture medium inside the reservoir of the cultivating vessel (10) to flow through the circulating space (31) to form a circulating flow loop.

When in use, an apparatus for carbon dioxide-capture system in accordance with the present invention is mounted in a dioxide-capturing system implemented by a sealed transparent chamber to cultivate micro-algae by a method for decreasing carbon dioxide in environment.

A method for using an apparatus according to the present invention to capture carbon dioxide is performed by the following steps: placing a micro-alga culture into a reservoir inside a cultivating vessel (10) of an apparatus for carbon dioxide-capturing device as described above in an environment containing carbon dioxide suitable for photosynthesis; transferring the micro-alga culture into a corresponding tray (40) by the circulating mechanism (50); allowing the micro-alga culture to flow through the spout (411) of one tray (40), dropping into an adjacent tray (40) in sequence, and converging in the reservoir of the cultivating vessel (10); and alternatively followed by agitating the culture medium in the reservoir by the flow-directing mechanism (60) to generate a flow in a desired direction inside the reservoir of the cultivating vessel (10) and to allow the culture medium evenly distributing in the reservoir and effectively absorbing carbon dioxide dissolved in the culture medium; or using a supply pipe (70) to supply a supplement nutrition into the micro alga culture in the reservoir of the cultivating vessel (10).

According to the present invention, the term "an environment containing carbon dioxide suitable for photosynthesis", refers to an environment comprising sunshine or an environment provided with light suitable for micro algae to utilize in a photosynthetic pathway.

According to the present invention, the micro-alga used hereby comprises photoplankton; preferably, *chlorella* sp.; and more preferably, *chlorella pyrenoidosa*.

According to the present invention, the micro-alga culture contains photoplankton, for example, but not limited to, *chlorella* sp. Preferably, the micro-alga culture contains *chlorella pyrenoidosa*.

According to the present invention, "supplemental nutrition" includes, but is not limited to solutions containing sources of salts, trace elements, nitrogen, phosphorous, potassium and combinations thereof required for growth of micro-algae and are well known in the art.

Experiments:

A solution containing 0.6 g urea, 0.21 g $KH_2PO_4$, 0.25 g $MgSO_4$, 0.025 g $FeSO_4.4H_2O$ and an adequate amount of trace element was used as culture medium for culturing *Chlorella* sp; *Chlorella pyrenoidosa* (provided by HONG KUANG MICROBE ENTERPRISE CO., LTD., Taiwan) strain of micro-algae was cultivated; the apparatus for carbon-dioxide capture system as disclosed was mounted in a hermitically sealed, transparent container as whole as a carbon-dioxide capture system with a capacity of about 1190 liters allowing the apparatus for carbon dioxide-capture system in accordance with the present invention to bask in sunshine or light; and an Infrared carbon dioxide sensor was used to determine concentration of carbon dioxide in the carbon dioxide-capture system every 60 seconds. A micro-algae culture with a volume of 30 L to 140 L was prepared and ready for use.

After being cultivated in vitro, micro-algae are transferred into a large-scale culture vessel (10) and cultured under aeration to obtain an alga culture with a concentration of 300 g dried algae per ton of the alga culture. Obtained alga culture was then transferred into the reservoir of the culturing vessel (10) and mounted in the apparatus for carbon dioxide-capture system as described above. The apparatus was placed at atmospheric pressure. The alga culture obtained as described above was pumped into the space in the corresponding tray (40) by the pump (51) through the introducing pipe (52), and flowed through the spout (411). The spout (411) guided the alga culture into the subsequent tray (40) as a waterfall forcing air into the alga culture for improved algae growth and the alga culture converged in the reservoir of the culturing vessel (10). The alga culture flowed into the reservoir circulated in a direction led by the propeller (62) of the flow-directing mechanism (60). The process described above was repeated for 2 hours. During the processes, micro-algae contacted with and absorbed carbon dioxide to allow micro-algae undergoing photosynthesis to consume carbon dioxide, grow and also generate oxygen.

The concentration of carbon dioxide in the device was determined by Infrared carbon dioxide sensor. Once a value of the concentration of carbon dioxide dropped to zero, the alga culture was collected, concentrated, dried and weighed to obtain a weight of the dried algae.

Figure 6:
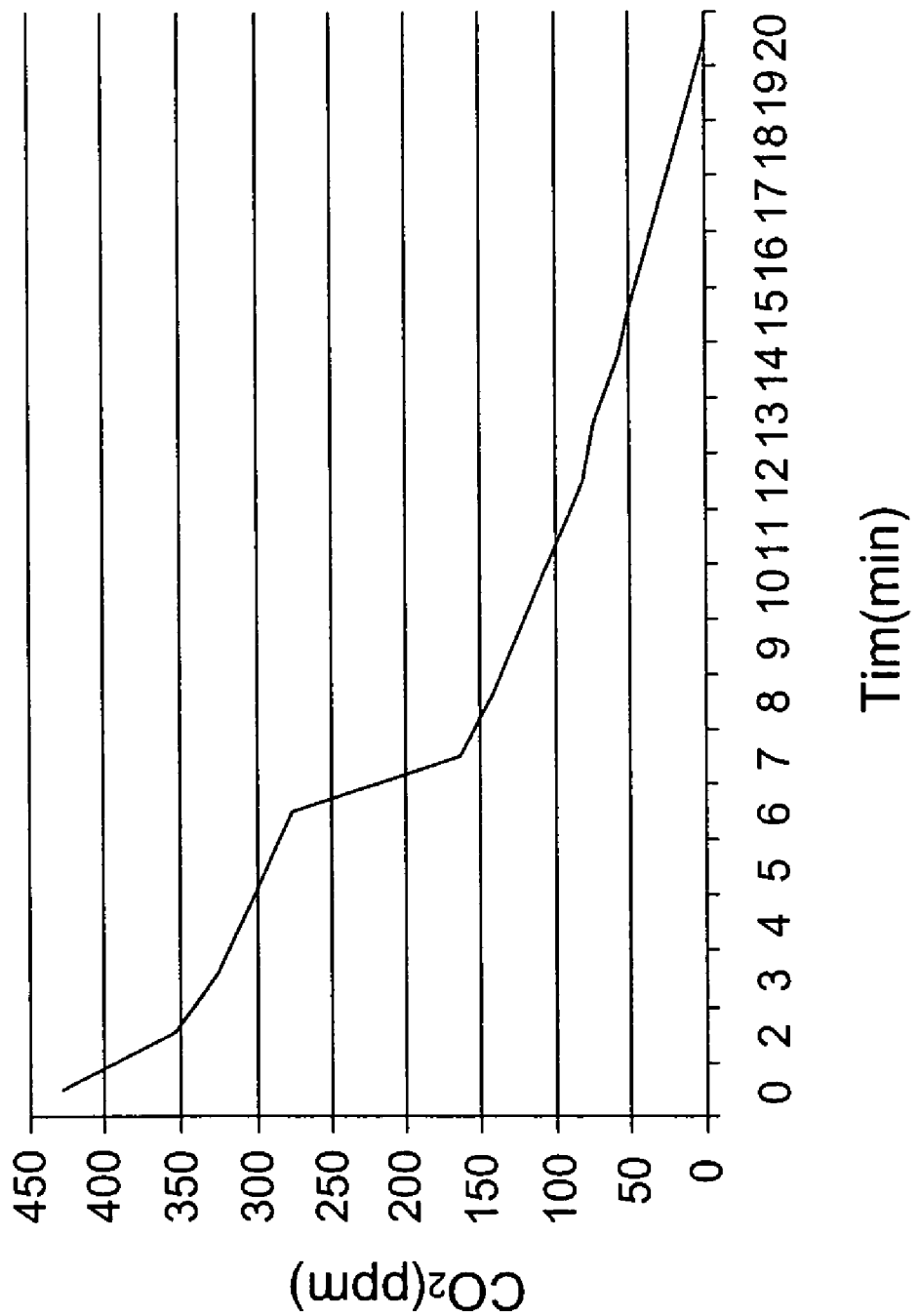
FIG. 6 illustrates a curve obtained by plotting the content of carbon dioxide in the carbon dioxide-capture system apparatus in FIG. 1 against time.

As shown in FIG. 6, a total amount of carbon dioxide fixed in the carbon-capturing device by 10.5 g of dried *Chlorella pyrenoidosa* was calculated as 0.9144 g. Therefore, in the apparatus in accordance with the present invention, 0.9144 g carbon dioxide was fixed every 19 minutes, extrapolating to 34.6499 g carbon dioxide fixed by 10.5 g dried *Chlorella pyrenoidosa* for 12 hours and 3.23 ton carbon dioxide fixed by one ton dried *Chlorella pyrenoidosa* every 12 hours.

In a preferred embodiment, the cultivating vessel (10) of the apparatus in accordance with the present invention used was 30 meters by a width of 6 meters for a liquid submerged culture of dried Chlorella pyrenoidosa at 26° C. under atmospheric pressure. The depth of the submerged culture was 56 cm, estimated as 100 ton of culture medium. 300 g dried *Chlorella pyrenoidosa* per ton of culture medium was inoculated as a large-scale culture. After 24 hours culture, the concentration of alga was monitored as 1120 g/ton, extrapolating to 112 kg of alga in 100 ton culture. That is, 166.5 kg of carbon dioxide fixed and 121.5 kg generated by a surface of submerged culture of 180 $m^2$ within 24 hours, extrapolating to 9250 kg carbon dioxide fixed by a surface of submerged culture of 1 hectare within a day and 3376 ton carbon dioxide fixed thereby within a year. The efficiency of carbon fixation is 135 times to that of trees planted within the same area.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An apparatus for a carbon dioxide-capture system comprising:
   a cultivating vessel,
   at least one basking mechanism, and
   a circulating mechanism,
   wherein the cultivating vessel comprises a body comprising an open container comprising an annular sidewall and a bottom defining a reservoir for accommodating culture medium;
   wherein each of the at least one basking mechanism comprises:

(1) a frame mounted in the reservoir on the bottom of the cultivating vessel, the frame comprising a top and a bottom, wherein the bottom comprises a circulating space to allow culture medium to flow through; and (2) multiple trays imbricately mounted on the frame at predetermined intervals, wherein each tray comprises:

(i) a panel being attached to the frame;

(ii) an overlap disposed above a panel of an adjacent tray; and (iii) at least one spout being formed through the tray at the overlap of the panel; and wherein the circulating mechanism comprises:

(1) a pump comprising:
an inlet communicating with the reservoir; and
an outlet;

(2) an introducing pipe connected to the outlet of the pump, wherein the introducing pipe comprises a distal end mounted over one of the trays of the basking mechanism; and (3) at least one orifice through the introducing pipe near the distal end, wherein the circulating mechanism is mounted in the cultivating vessel and trays.

2. The apparatus of claim 1, further comprising:
at least one supply pipe attached to the cultivating vessel, each supply pipe comprises:
a charging end disposed across the reservoir of the cultivating vessel; and
at least one medium-supplying hole formed on the charging end.

3. The apparatus of claim 1, further comprising at least one flow-directing mechanism attached to the cultivating vessel and mounted across the reservoir.

4. The apparatus of claim 3, wherein each one of the at least one flow-directing mechanism comprises:

a drive shaft attached rotatably to the cultivating vessel; and at least one propeller mounted on the drive shaft, wherein rotation of the drive shaft induces the at least one propeller to disturb the culture medium to generate a flow in a desired direction inside the reservoir of the cultivating vessel and to increase contact between the culture medium and $CO_2$ in air.

5. The apparatus of claim 3, wherein the cultivating vessel further comprises:

a central barrier mounted in the reservoir on the bottom of the cultivating vessel, the central barrier comprising two sidewalls, wherein the annular sidewall and the bottom of the body and the sidewalls of the barrier define the reservoir of the cultivating vessel; and wherein the frame in each of the at least one basking mechanism is mounted between the annular sidewall of the body and a corresponding sidewall of the barrier.

6. The apparatus of claim 5, wherein each tray further comprises:

a rim protruding from the panel and having
an outer surface; and
an inner surface defining a space for accommodating the culture medium in combination with the panel.

7. The apparatus of claim 6, wherein the frame in each of the at least one basking mechanism comprises two supports extending from the top to the bottom of the frame, wherein the supports are attached to the body and the barrier of the cultivating vessel, respectively, thereby defining the circulating space, and wherein the outer surface of the rim of each tray is attached to the frame of a corresponding basking mechanism.

* * * * *